United States Patent
Cheminet et al.

(10) Patent No.: US 9,108,069 B2
(45) Date of Patent: Aug. 18, 2015

(54) POLYMERIC DEPILATORY COMPOSITION WITH CONTROLLED TEMPERATURE SETTING OF USE

(75) Inventors: Helena Cheminet, Gradignan (FR); Ali Ben Moussa, Bordeaux (FR); Virginie Fera, Cergy (FR); Hubert Delagneau, Mainvilliers (FR)

(73) Assignee: CHURCH & DWIGHT CO., INC., Princeton, NJ (US)

( * ) Notice: Subject to any disclaimer, the term of this patent is extended or adjusted under 35 U.S.C. 154(b) by 1050 days.

(21) Appl. No.: 12/531,239

(22) PCT Filed: Mar. 14, 2008

(86) PCT No.: PCT/US2008/057009
§ 371 (c)(1),
(2), (4) Date: Oct. 29, 2009

(87) PCT Pub. No.: WO2008/115794
PCT Pub. Date: Sep. 25, 2008

(65) Prior Publication Data
US 2010/0040571 A1    Feb. 18, 2010

(30) Foreign Application Priority Data
Mar. 16, 2007    (FR) .................... 07 53878

(51) Int. Cl.
*A61K 8/72* (2006.01)
*A61Q 9/04* (2006.01)
*A61K 8/31* (2006.01)
*A61K 8/81* (2006.01)
*A61K 8/85* (2006.01)
*A61K 8/92* (2006.01)

(52) U.S. Cl.
CPC ... *A61Q 9/04* (2013.01); *A61K 8/31* (2013.01); *A61K 8/8135* (2013.01); *A61K 8/85* (2013.01); *A61K 8/922* (2013.01); *A61K 2800/544* (2013.01)

(58) Field of Classification Search
None
See application file for complete search history.

(56) References Cited

U.S. PATENT DOCUMENTS

| | | | |
|---|---|---|---|
| 2,425,696 A | 8/1947 | Herrmann et al. | |
| 4,282,877 A * | 8/1981 | Mathews | 606/134 |
| 5,154,919 A | 10/1992 | Des Garets | |
| 5,273,757 A * | 12/1993 | Jaeger et al. | 424/448 |
| 5,449,519 A * | 9/1995 | Wolf et al. | 424/401 |
| 7,569,615 B2 | 8/2009 | Leinweber et al. | |
| 2004/0120915 A1 | 6/2004 | Yang et al. | |
| 2004/0180014 A1* | 9/2004 | Gupta | 424/70.1 |
| 2007/0031360 A1 | 2/2007 | Gupta | |

FOREIGN PATENT DOCUMENTS

| | | |
|---|---|---|
| DE | 10329723 B3 | 12/2004 |
| EP | 299816 A1 | 1/1989 |
| FR | 2751872 A1 | 2/1998 |
| GB | 1348760 A | 3/1974 |
| WO | 2005112876 A1 | 12/2005 |

OTHER PUBLICATIONS

Beszedes et al. (Annals of Faculty Engineering Hunedoara International Journal of Engineering (2012).*

* cited by examiner

*Primary Examiner* — Patricia A Duffy
*Assistant Examiner* — Garen Gotfredson
(74) *Attorney, Agent, or Firm* — Fishman & Associates, LLC

(57) ABSTRACT

The object of the invention is a polymeric depilatory (epilatory) composition including: a. at least one basic compound permitting adherence to the hair, b. at least one wax-based rheology regulating compound, and c. at least one microwave absorber compound.

6 Claims, 2 Drawing Sheets

POLYMERIC DEPILATORY COMPOSITION WITH CONTROLLED TEMPERATURE SETTING OF USE

CROSS-REFERENCE TO RELATED APPLICATION

This application is related to French Patent Application Serial No. 07/53878 filed Mar. 16, 2007 and takes priority therefrom.

FIELD OF THE INVENTION

This invention concerns a depilatory (epilatory) polymeric composition with controlled temperature setting of use. The novel depilatory/epilatory polymeric composition is directly applicable to the skin with removal by peeling, preferentially without an additional support strip.

BACKGROUND OF THE INVENTION

A well known principle permits enclosure of hair in a polymeric matrix in the form of a strip and the manual removal of the strip by peeling to ensure hair extraction. For reasons of depilatory effectiveness, non aqueous polymeric compositions are generally preferred. Nevertheless, the requirements these depilatory polymeric compositions must meet are numerous and, for some, difficult to reconcile.

One requirement is to be able to bring and maintain the depilatory polymeric composition during the depilation process to a temperature adapted to provide the desired temperature in a fast and practical way.

Another important factor is the time for depilation duration, which time needs to be reduced because the depilation practice is tedious, and professionals as well as consumers wish to dedicate the least possible time to it.

Also, not only should the heating time be reduced, but the duration for which the polymeric depilatory composition remains usable during the depilation process should be the longest possible. Such duration of use is the interval during which the depilatory polymeric composition remains at a temperature acceptable for the skin, that is compatible with its homogeneous, easy and painless application, in a thin layer with a spatula or any appropriated applicator in order to be able to enclose the hair to be pulled. Currently, the duration of use, according to the here above-defined meaning, is in the order of 10 minutes for a 400 g pot of composition formulated according to the prior art.

Aesthetic criteria are important in that they can contribute to regular epilation practices; in addition, the epilatory polymeric compositions should also help to improve the overall experience of epilation by being able to adhere to short hair, therefore improving the epilation quality. The adherence of the composition to the hair has been incorporated into the formulation so as to obtain a very satisfactory and immediate high quality epilation, leaving only minimally visible, less numerous and shorter hair. Such improvement of the adherence also offers the possibility to proceed with a new epilation on short hair without having to wait for hair to regrow to a significant and unsightly length.

A depilatory polymeric composition must also meet other important requirements, regarding its rheology. Indeed, it is necessary to apply the depilatory polymeric composition in a thin layer, at a temperature acceptable for sensitive areas of the skin, without provoking the formation of threads susceptible to disrupt handling. Once the wax is frozen on the skin and the hair enclosed, it is essential that the strip produced be removed by hand, by peeling, in a single, fast movement. This entails that the laid strip should keep a certain deformability, suppleness and flexibility. On the other hand, these parameters must remain within values that do not affect negatively the cohesion of said strip and avoid stretching, making the removal of the strip difficult and risking the formation of composition deposits or residues adhering to the skin, which residues are always difficult and unpleasant to eliminate from the skin. In particular, for compositions forming strips on the skin, the composition rheology should be adapted to permit strip removal when the composition reaches a temperature at which the strip surface no longer adheres to the finger, i.e. a temperature at which the strip adheres minimally to the skin while keeping the required abilities for adhering to the hair.

Considering the intended use of the product, the depilatory polymeric composition may include at least dyes and/or perfumes for the sake of aesthetics. It is also possible to include solid particles or fibers, or ingredients intended notably to modify the presentation or aspect.

The prior art proposed depilatory waxes as described in French patent No. 2 751 872. However, such waxes only very partially met the requirements recited above, not permitting namely a homogeneous heating by a microwave heating oven.

Another European patent EP No. 299 816 proposed a rosin and elastomer-based depilatory composition of a disposable type. That patent, although not providing sufficient information, is characterized by the combination of an elastomeric or thermoplastic macromolecular compound, rosin and a plasticizer.

This invention proposes a depilatory polymeric composition that meets the numerous requirements described above, that is industrially feasible, comfortable to apply, and easy to use by consumers.

DETAILED DESCRIPTION OF THE INVENTION

Figure 1:
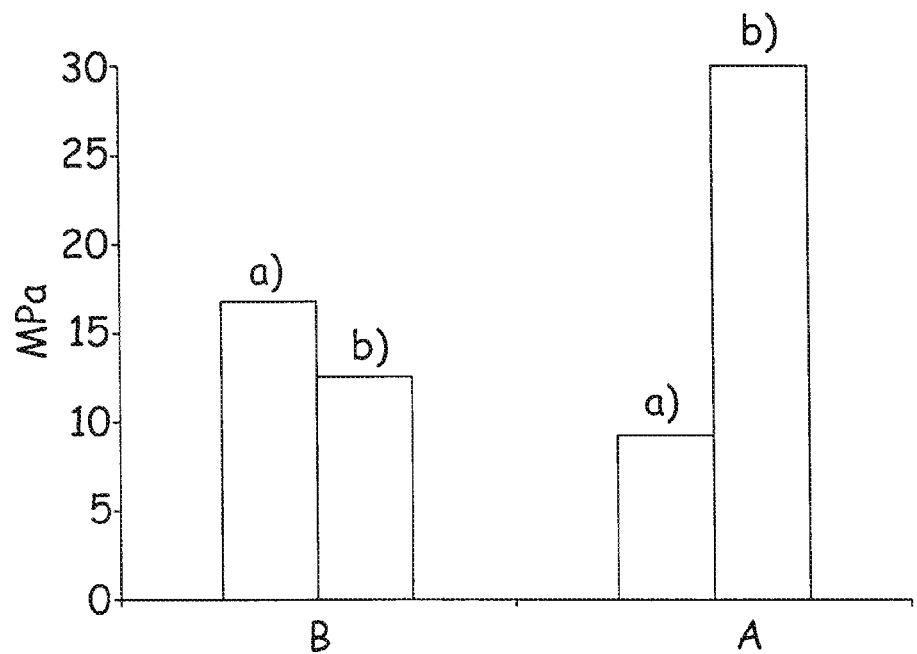
FIG. 1 is a comparative bar graph of two mechanical parameters, i.e., Young's modulus (a) and maximal distortion (b) for the composition A of this invention and the composition B of the prior art.

The invention is now described in detail through illustrative examples and line diagrams attached as drawings.

According to a particular, non limiting example, the depilatory polymeric composition according to the invention includes
  a. at least one basic compound including at least one resin for adherence to the hair,
  b. at least one rheology regulating compound, and
  c. at least one microwave absorber compound.

A basic compound a) is adapted possibly from derivatives of natural products such as pine resin, or esterified rosin. This compound is complex and includes notably abietic acid so that it can be esterified with various polyols, which notably makes the fusion temperature vary.

In one embodiment, the modified rosin retained should be usable within a temperature range from 30 to 60° C., for example.

The basic compound of a) can also come from synthetic resins.

A useful product that may be found is a commercially formed modified rosin under the tradename Resiester, (Union Resinera), Uniontown, Ohio. Its main property is hair adherence.

Rheology regulating compound b) is a wax.

One can mention as products commercially available, a paraffin wax of the Luzafine series made by Kompass (France) and distributed by Baker Petrolite (France). Said wax presents low tackiness.

The combination of a) and b) would result in a brittle product, difficult to heat by means of microwave, and the heating homogeneity of the combination would not be particularly useful.

Compound c) is chosen from a polymer family with a dendritic structure, i.e. a hyper-branched polymer, or a dendritic polymer with very regular and symmetrical branched out structure. Therefore, the term dendritic is used for this family.

A dendritic polymer presents an architecture with a central poly-functional core and a tree-like structure with identical patterns. After ramification, a spherical type of structure is obtained, provided with many reactive terminal functions.

Following the chemical nature of dendritic polymers, if the present chemical functions are polar, this architecture confers to these dendritic polymers, properties such as:
(1) strong microwave absorption capacity from the presence of many dipoles,
(2) excellent distribution and diffusion of the energy contributed by the microwaves since the dipoles are themselves distributed spatially and in a homogeneous way,
(3) strong adherence to hair thanks to peripheral reactive groups,
(4) providing a strip, by cohesion of the molecular mass.

One finds commercially useful dendritic polymers under the tradename Boltorn, Perstop Polyols, Toledo, Ohio.

The dendritic polymers present the advantages listed above without affecting the qualities and properties expected from the other compounds.

According to an improvement of compositions a), b) and c) of the invention, one can advantageously associate to basic compound a), a vinyl ethylene/acetate linear structure copolymer that is thermoplastic in a medium polarity form called hypocrystalline. Such copolymer is marketed notably under the commercial name EVATANE®, Arkema Canada, Inc., Ontario.

Another regulating compound usable in association with paraffin wax constituting compound b) is a hypocrystalline wax from refined petroleum with a high percentage of isoparaffinic hydrocarbons and naphthenic hydrocarbons. The hypocrystalline structure of such wax is constituted of small size patterns that make it more flexible than paraffin wax.

According to this invention, a particularly useful depilatory composition includes:
Compound a):
    between 40 and 70% Resiester,™
    between 10 and 25% Evatane,™
Compound b):
    between 4 and 20% paraffin wax Luzafine.™
Compound c)
    between 5 and 25% dendritic polymer Boltorn,™
A depilatory composition providing particularly satisfactory results includes:
Compound a):
    between 50 and 60% Resiester,™
    between 15 and 20% Evatane,™
Compound b):
    between 6 and 12% Luzafine,™
Compound c)
    between 15 and 20% Boltorn.™

EXAMPLE

The results obtained with this last composition provide a confirmation for reaching qualities intrinsically sought-after and in relation to one of the commercial depilatory compositions containing:
    Basic resins: 78%
    Vinyl ethylene—acetate copolymer 9%
    Paraffins: 13%

One may also consider compositions presenting solidification points at low temperature of about 30° C., requiring a solid support such as a piece of material, a non-woven, a rosin to permit the removal of the strip with hair.

Heating

At a same microwave power, the preparation time of the depilatory composition according to this invention is decreased, compared to the existing depilatory composition. For a comparable quantity by weight, the time is decreased by about 30%. With the composition according to the invention: the heating time itself is reduced, the waiting time for temperature static homogenization without mixing is strongly reduced and the dynamic mixing time remains identical.

Heating is homogeneous and the whole volume decreases in viscosity without forming pockets, and without case hardening phenomenon.

Small residual quantities of the composition on the walls or bottom of the container or on the application devices at the end of use remain usable because the microwaves ensure an homogeneous temperature to all quantities.

It is the result of the very strong polarity of the dendritic polymer, made of carbon but also of heteroatom constituting bipolar systems. This strong polarity greatly improves the engagement of the composition on the hair, which is also polar.

Balance Between Cohesion and Flexibility:

Cohesion is an important parameter because possible residues from the depilatory composition are difficult to remove, and it is important to keep a monolithic strip.

Nevertheless, flexibility is necessary to permit the removal by peeling.

FIG. 1 shows the comparison of composition B of the prior art and composition A according to the invention.

Young's modulus a) (capacity to be distorted elastically: the weaker the module, the more the distortion), and
    the maximal distortion b) (maximal distortion before breakage).

One notes that the maximal distortion before breakage is nearly doubled, thanks notably to the globular form of the dendritic polymer patterns.

Young's modulus decreases, which corroborates the distortion improvement before breakage.

Figure 2:
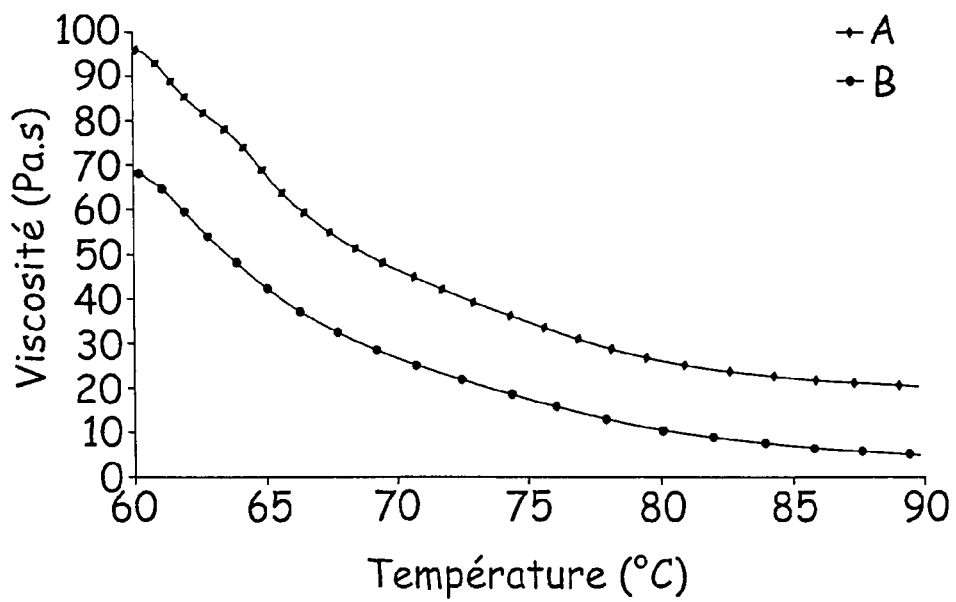
FIG. 2 is a comparative line graph of viscosity as a function of temperature, for a product (B) of the prior art and for the composition (A) according to the present invention.

Viscosity:

FIG. 2 shows the comparative curves of Theological measures: viscosity is increased leading to a better consistency and a better applicability.

In A, are represented the viscosity line graph as a function of temperature of the composition according to the invention, and in B the viscosity line graph as a function of temperature of the marketed depilatory composition mentioned above.

Nonetheless, it is necessary to also allow a mechanical mixing when exiting the oven in the container before usage and this mixing should not be too difficult.

Maintaining Temperature.

Figure 3:
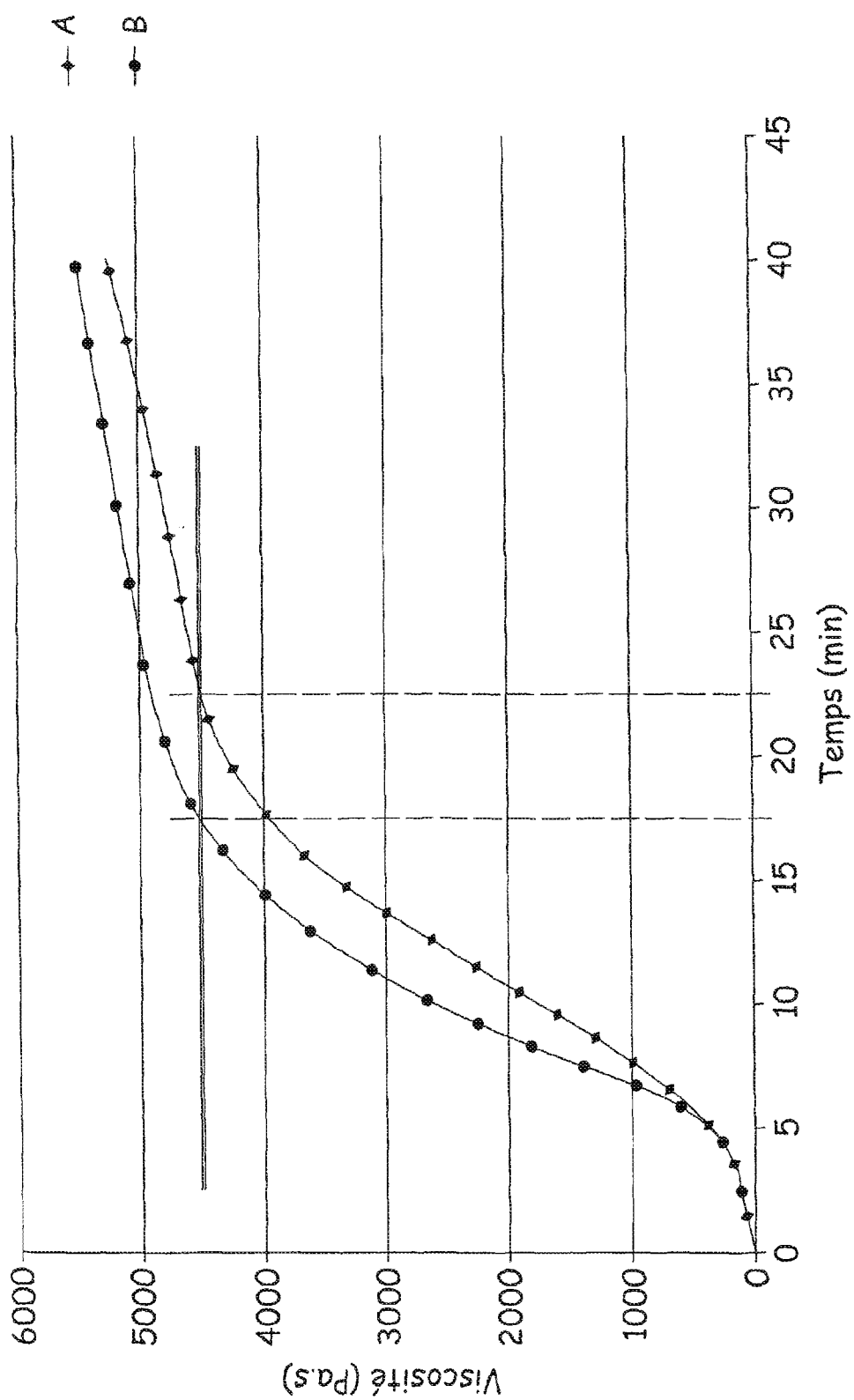
FIG. 3 is a comparative of cooling curves at given viscosity for a composition of the prior art (B) and of this invention (A).

The depilatory composition according to the invention presents a cooling rate close to 30% lower than the comparative composition as shown in FIG. 3.

In A, the viscosity line graph as a function of time of the composition according to the invention, and in B the viscosity line graph as a function of time of the marketed depilatory composition mentioned above.

The duration of use is therefore extended, in the example with a viscosity equal to 4500 Pa·s, a 5 min gain. The number of reheatings is therefore reduced.

The invention claimed is:

1. A depilatory polymeric composition comprising:
   a): at least one basic compound permitting adherence to the hair, the basic compound being a rosin in the amount of 40-70%,
   b): at least one wax-based rheology regulating compound in the amount of 4-20%, and
   c): at least one microwave absorber compound in the amount of between 5 and 25% of said composition, said microwave absorber compound being a dendritic polymer.

2. The depilatory polymeric composition according to claim 1, wherein the at least one wax-based rheology regulating compound is a paraffin wax.

3. The depilatory polymeric composition according to claim 2, wherein the at least one wax-based rheology regulating compound further includes a hypocrystalline wax.

4. The depilatory polymeric composition according to claim 1, comprising
   the rosin in the amount of between 50 and 60%,
   the at least one wax in the amount of between 6 and 12%,
   the dendritic polymer in the amount of between 15 and 20%, and further comprising a semi-crystalline thermoplastic polymer in the amount of between 15 and 20% of said composition.

5. A method of removing hair comprising: applying onto hair to be removed a melted depilatory composition of claim 1,
   allowing the applied melted composition to harden, and then removing the hardened composition.

6. The method of claim 5, wherein the depilatory composition is melted by heating said composition in a microwave oven.

* * * * *